US010342611B2

United States Patent
Rioux

(10) Patent No.: US 10,342,611 B2
(45) Date of Patent: *Jul. 9, 2019

(54) CAVITARY TISSUE ABLATION

(71) Applicant: Innoblative Designs, Inc., Chicago, IL (US)

(72) Inventor: Robert F. Rioux, Ashland, MA (US)

(73) Assignee: Innoblative Designs, Inc., Chicago, IL (US)

( * ) Notice: Subject to any disclaimer, the term of this patent is extended or adjusted under 35 U.S.C. 154(b) by 250 days.

This patent is subject to a terminal disclaimer.

(21) Appl. No.: 15/142,616

(22) Filed: Apr. 29, 2016

(65) Prior Publication Data
US 2016/0317221 A1 Nov. 3, 2016

Related U.S. Application Data

(60) Provisional application No. 62/154,377, filed on Apr. 29, 2015.

(51) Int. Cl.
*A61B 18/14* (2006.01)
*A61B 18/00* (2006.01)

(52) U.S. Cl.
CPC .. *A61B 18/1492* (2013.01); *A61B 2018/0016* (2013.01); *A61B 2018/00083* (2013.01); *A61B 2018/00238* (2013.01); *A61B 2018/00255* (2013.01); *A61B 2018/00267* (2013.01); *A61B 2018/00333* (2013.01); *A61B 2018/00452* (2013.01); *A61B 2018/00505* (2013.01); *A61B 2018/00529* (2013.01); *A61B 2018/00541* (2013.01); *A61B 2018/00547* (2013.01); *A61B 2018/00559* (2013.01);

(Continued)

(58) Field of Classification Search
CPC .... A61B 2018/1467; A61B 2018/1472; A61B 2218/002; A61B 2018/0022; A61B 2018/0025; A61B 2018/00255
See application file for complete search history.

(56) References Cited

U.S. PATENT DOCUMENTS

| 4,699,147 A | 10/1987 | Chilson et al. |
| 4,976,711 A | 12/1990 | Parins et al. |

(Continued)

FOREIGN PATENT DOCUMENTS

| CN | 2610858 Y | 4/2004 |
| CN | 104546124 A | 4/2015 |

(Continued)

OTHER PUBLICATIONS

International Search Report and Written Opinion of the International Searching Authority dated Aug. 22, 2016 for International Application No. PCT/US2016/030081 (11 Pages).

(Continued)

*Primary Examiner* — Jaymi E Della
(74) *Attorney, Agent, or Firm* — Brown Rudnick LLP

(57) ABSTRACT

The invention relates to a tissue ablation system including an ablation device having a deployable applicator head configured to be delivered to a tissue cavity and ablate marginal tissue surrounding the tissue cavity. The deployable applicator head is configured to be delivered to a tissue cavity while in a collapsed configuration and ablate marginal tissue surrounding the tissue cavity while in an expanded configuration.

5 Claims, 12 Drawing Sheets

(52) U.S. Cl.
CPC ............. *A61B 2018/00577* (2013.01); *A61B 2018/144* (2013.01); *A61B 2018/1467* (2013.01); *A61B 2018/1472* (2013.01); *A61B 2218/002* (2013.01)

(56) References Cited

U.S. PATENT DOCUMENTS

| | | | |
|---|---|---|---|
| 4,979,948 A | 12/1990 | Geddes et al. |
| 5,045,056 A | 9/1991 | Behl |
| 5,100,423 A | 3/1992 | Fearnot |
| 5,117,828 A | 6/1992 | Metzger et al. |
| 5,334,193 A | 8/1994 | Nardella |
| 5,429,605 A | 7/1995 | Richling et al. |
| 5,471,982 A | 12/1995 | Edwards et al. |
| 5,472,441 A | 12/1995 | Edwards et al. |
| 5,486,161 A | 1/1996 | Lax et al. |
| 5,536,267 A | 7/1996 | Edwards et al. |
| 5,562,720 A | 10/1996 | Stern et al. |
| 5,657,760 A | 8/1997 | Ying et al. |
| 5,672,153 A | 9/1997 | Lax et al. |
| 5,672,173 A | 9/1997 | Gough et al. |
| 5,672,174 A | 9/1997 | Gough et al. |
| 5,683,384 A | 11/1997 | Gough et al. |
| 5,713,942 A | 2/1998 | Stern et al. |
| 5,728,143 A | 3/1998 | Gough et al. |
| 5,772,590 A | 6/1998 | Webster, Jr. |
| 5,782,827 A | 7/1998 | Gough et al. |
| 5,827,276 A | 10/1998 | LeVeen et al. |
| 5,840,076 A | 11/1998 | Swanson et al. |
| 5,846,239 A | 12/1998 | Swanson et al. |
| 5,855,576 A | 1/1999 | LeVeen et al. |
| 5,863,290 A | 1/1999 | Gough et al. |
| 5,868,736 A | 2/1999 | Swanson et al. |
| 5,868,776 A | 2/1999 | Wright |
| 5,871,483 A | 2/1999 | Jackson et al. |
| 5,888,198 A | 3/1999 | Eggers et al. |
| 5,891,136 A | 4/1999 | McGee et al. |
| 5,893,847 A | 4/1999 | Kordis |
| 5,913,855 A | 6/1999 | Gough et al. |
| 5,928,229 A | 7/1999 | Gough et al. |
| 5,935,123 A | 8/1999 | Edwards et al. |
| 5,961,513 A | 10/1999 | Swanson et al. |
| 5,980,517 A | 11/1999 | Gough |
| 6,009,877 A | 1/2000 | Edwards |
| 6,032,077 A | 2/2000 | Pomeranz |
| 6,036,689 A | 3/2000 | Tu et al. |
| 6,053,913 A | 4/2000 | Tu et al. |
| 6,053,937 A | 4/2000 | Edwards et al. |
| 6,063,081 A | 5/2000 | Mulier et al. |
| 6,071,278 A | 6/2000 | Panescu et al. |
| 6,071,280 A | 6/2000 | Edwards et al. |
| 6,099,526 A | 8/2000 | Whayne et al. |
| 6,112,123 A | 8/2000 | Kelleher et al. |
| 6,123,718 A | 9/2000 | Tu et al. |
| 6,142,993 A | 11/2000 | Whayne et al. |
| 6,221,071 B1 | 4/2001 | Sherry et al. |
| 6,241,666 B1 | 6/2001 | Pomeranz et al. |
| 6,251,109 B1 | 6/2001 | Hassett et al. |
| 6,258,087 B1 | 7/2001 | Edwards et al. |
| 6,309,352 B1 | 10/2001 | Oraevsky et al. |
| 6,312,408 B1 | 11/2001 | Eggers et al. |
| 6,312,429 B1 | 11/2001 | Burbank et al. |
| 6,358,248 B1 | 3/2002 | Mulier et al. |
| 6,379,353 B1 | 4/2002 | Nichols |
| 6,409,722 B1 | 6/2002 | Hoey et al. |
| 6,425,877 B1 | 7/2002 | Edwards |
| 6,454,766 B1 | 9/2002 | Swanson et al. |
| 6,491,710 B2 | 12/2002 | Satake |
| 6,494,902 B2 | 12/2002 | Hoey et al. |
| 6,503,247 B2 | 1/2003 | Swartz et al. |
| 6,522,930 B1 | 2/2003 | Schaer et al. |
| 6,537,248 B2 | 3/2003 | Mulier et al. |
| 6,537,272 B2 | 3/2003 | Christopherson et al. |
| 6,544,262 B2 | 4/2003 | Fleischman |
| 6,551,310 B1 | 4/2003 | Ganz et al. |
| 6,585,732 B2 | 7/2003 | Mulier et al. |
| 6,623,481 B1 | 9/2003 | Garbagnati et al. |
| 6,638,275 B1 | 10/2003 | McGaffigan et al. |
| 6,648,883 B2 | 11/2003 | Francischelli et al. |
| 6,663,622 B1 | 12/2003 | Foley et al. |
| 6,692,466 B1 | 2/2004 | Chow et al. |
| 6,736,810 B2 | 5/2004 | Hoey et al. |
| 6,736,811 B2 | 5/2004 | Panescu et al. |
| 6,743,226 B2 | 6/2004 | Cosman et al. |
| 6,764,487 B2 | 7/2004 | Mulier et al. |
| 6,780,183 B2 | 8/2004 | Jimenez, Jr. et al. |
| 6,805,131 B2 | 10/2004 | Kordis |
| 6,826,421 B1 | 11/2004 | Beatty et al. |
| 6,849,073 B2 | 2/2005 | Hoey et al. |
| 6,872,206 B2 | 3/2005 | Edwards et al. |
| 6,878,149 B2 | 4/2005 | Gatto |
| 6,955,641 B2 | 10/2005 | Lubock |
| 6,978,788 B2 | 12/2005 | Klimberg et al. |
| 6,984,232 B2 | 1/2006 | Vanney et al. |
| 7,104,989 B2 | 9/2006 | Skarda |
| 7,150,745 B2 | 12/2006 | Stern et al. |
| 7,156,845 B2 | 1/2007 | Mulier et al. |
| 7,169,144 B2 | 1/2007 | Hoey et al. |
| 7,247,155 B2 | 7/2007 | Hoey et al. |
| 7,276,061 B2 | 10/2007 | Schaer et al. |
| 7,306,593 B2 | 12/2007 | Keidar et al. |
| 7,326,208 B2 | 2/2008 | Vanney et al. |
| 7,344,535 B2 | 3/2008 | Stern et al. |
| 7,364,579 B2 | 4/2008 | Mulier et al. |
| 7,367,972 B2 | 5/2008 | Francischelli et al. |
| 7,371,231 B2 | 5/2008 | Rioux et al. |
| 7,399,299 B2 | 7/2008 | Daniel et al. |
| 7,416,552 B2 | 8/2008 | Paul et al. |
| 7,419,489 B2 | 9/2008 | Vanney et al. |
| 7,556,628 B2 | 7/2009 | Utley et al. |
| 7,632,268 B2 | 12/2009 | Edwards et al. |
| 7,717,909 B2 | 5/2010 | Strul et al. |
| 7,769,432 B2 | 8/2010 | Klimberg et al. |
| 7,776,034 B2 | 8/2010 | Kampa |
| 7,828,793 B2 | 11/2010 | Thompson et al. |
| 7,862,498 B2 | 1/2011 | Nguyen et al. |
| 7,879,030 B2 | 2/2011 | Paul et al. |
| 7,942,873 B2 | 5/2011 | Kwan |
| 7,959,628 B2 | 6/2011 | Schaer et al. |
| 7,959,631 B2 | 6/2011 | DiCarlo |
| 8,034,022 B2 | 10/2011 | Boatman |
| 8,043,289 B2 | 10/2011 | Behl et al. |
| 8,048,069 B2 | 11/2011 | Skwarek et al. |
| 8,114,071 B2 | 2/2012 | Woloszko et al. |
| 8,224,416 B2 | 7/2012 | de la Rama et al. |
| 8,303,584 B2 | 11/2012 | Burdio Pinilla et al. |
| 8,388,573 B1 | 3/2013 | Cox |
| 8,398,624 B2 | 3/2013 | Rioux et al. |
| 8,409,193 B2 | 4/2013 | Young et al. |
| 8,444,638 B2 | 5/2013 | Woloszko et al. |
| 8,465,484 B2 | 6/2013 | Davalos et al. |
| 8,465,486 B2 | 6/2013 | Danek et al. |
| 8,588,886 B2 | 11/2013 | de la Rama et al. |
| 8,591,461 B2 | 11/2013 | Boatman |
| 8,617,158 B2 | 12/2013 | Garabedian et al. |
| 8,647,339 B2 | 2/2014 | Satake |
| 8,657,814 B2 | 2/2014 | Werneth et al. |
| 8,734,439 B2 | 5/2014 | Gough et al. |
| 8,814,855 B2 | 8/2014 | DiCarlo et al. |
| 8,834,461 B2 | 9/2014 | Werneth et al. |
| 8,979,838 B2 | 3/2015 | Woloszko et al. |
| 8,979,841 B2 | 3/2015 | Kunis et al. |
| 9,078,665 B2 | 7/2015 | Moss et al. |
| 9,131,980 B2 | 9/2015 | Bloom |
| 9,839,472 B2 | 12/2017 | Rioux et al. |
| 9,848,936 B2 | 12/2017 | Rioux et al. |
| 9,855,098 B2 | 1/2018 | Rioux |
| 2001/0031941 A1 | 10/2001 | Edwards et al. |
| 2002/0026186 A1 | 2/2002 | Woloszko et al. |
| 2002/0062123 A1 | 5/2002 | McClurken et al. |
| 2002/0087208 A1 | 7/2002 | Koblish et al. |
| 2002/0095152 A1 | 7/2002 | Ciarrocca et al. |
| 2002/0115992 A1 | 8/2002 | Utley et al. |
| 2002/0120259 A1 | 8/2002 | Lettice et al. |

(56) References Cited

U.S. PATENT DOCUMENTS

| | | |
|---|---|---|
| 2003/0009166 A1 | 1/2003 | Moutafis et al. |
| 2003/0036680 A1 | 2/2003 | Black |
| 2003/0130711 A1 | 7/2003 | Pearson et al. |
| 2003/0225403 A1 | 12/2003 | Woloszko et al. |
| 2004/0087936 A1 | 5/2004 | Stern et al. |
| 2004/0092960 A1 | 5/2004 | Abrams et al. |
| 2005/0049454 A1 | 3/2005 | Ouchi |
| 2005/0154386 A1 | 7/2005 | West et al. |
| 2006/0212032 A1 | 9/2006 | Daniel et al. |
| 2006/0259027 A1 | 11/2006 | Kwan et al. |
| 2007/0083195 A1 | 4/2007 | Werneth et al. |
| 2008/0004534 A1 | 1/2008 | Gelbart et al. |
| 2008/0015565 A1 | 1/2008 | Davison |
| 2008/0103494 A1 | 5/2008 | Rioux et al. |
| 2009/0171340 A1 | 7/2009 | Young |
| 2009/0292177 A1 | 11/2009 | Eggers et al. |
| 2009/0299355 A1* | 12/2009 | Bencini ............... A61B 18/02 606/21 |
| 2010/0114087 A1 | 5/2010 | Edwards et al. |
| 2010/0256629 A1 | 10/2010 | Wylie et al. |
| 2011/0172485 A1 | 7/2011 | Lubock |
| 2011/0257646 A1 | 10/2011 | Utley et al. |
| 2012/0029510 A1 | 2/2012 | Haverkost |
| 2012/0059437 A1 | 3/2012 | Shalev |
| 2012/0109250 A1 | 5/2012 | Cates et al. |
| 2012/0172680 A1 | 7/2012 | Gelfand et al. |
| 2013/0085493 A1 | 4/2013 | Bloom et al. |
| 2013/0158536 A1 | 6/2013 | Bloom |
| 2013/0172870 A1 | 7/2013 | Germain et al. |
| 2013/0184702 A1 | 7/2013 | Neal, II et al. |
| 2013/0253506 A1* | 9/2013 | Rioux ............... A61B 18/1492 606/41 |
| 2013/0310833 A1 | 11/2013 | Brown et al. |
| 2013/0338662 A1 | 12/2013 | Weber |
| 2014/0018788 A1 | 1/2014 | Engelman et al. |
| 2014/0018794 A1* | 1/2014 | Anderson .......... A61B 18/1492 606/41 |
| 2014/0031810 A1 | 1/2014 | Mahvi et al. |
| 2014/0058376 A1 | 2/2014 | Horn et al. |
| 2014/0221998 A1 | 8/2014 | Latterell |
| 2014/0276731 A1 | 9/2014 | Voegele et al. |
| 2014/0276748 A1 | 9/2014 | Ku et al. |
| 2014/0378960 A1 | 12/2014 | Fischer et al. |
| 2015/0018817 A1 | 1/2015 | Willard |
| 2015/0141982 A1 | 5/2015 | Lee |
| 2016/0113707 A1 | 4/2016 | Sahakian et al. |
| 2016/0113708 A1 | 4/2016 | Moss et al. |
| 2016/0184008 A1 | 6/2016 | Papaioannou et al. |
| 2016/0317221 A1 | 11/2016 | Rioux |
| 2017/0000559 A1 | 1/2017 | Rioux et al. |
| 2017/0027633 A1 | 2/2017 | Wham et al. |
| 2017/0119454 A1 | 5/2017 | Rioux et al. |
| 2017/0172646 A1 | 6/2017 | Patel et al. |
| 2017/0215947 A1 | 8/2017 | Rioux et al. |
| 2017/0215951 A1 | 8/2017 | Wang et al. |
| 2017/0252092 A1 | 9/2017 | Rioux et al. |
| 2017/0281267 A1 | 10/2017 | Rioux et al. |
| 2017/0281271 A1 | 10/2017 | Rioux |
| 2018/0014880 A1 | 1/2018 | Rioux et al. |
| 2018/0078305 A1 | 3/2018 | Rioux et al. |
| 2018/0104004 A1 | 4/2018 | Rioux et al. |

FOREIGN PATENT DOCUMENTS

| | | |
|---|---|---|
| DE | 102010032932 A1 | 2/2012 |
| EP | 0777445 B1 | 6/1999 |
| EP | 2942023 A3 | 2/2016 |
| JP | 3009735 B2 | 2/2000 |
| WO | 9510326 A1 | 4/1995 |
| WO | 9942047 A1 | 8/1999 |
| WO | 0051683 A1 | 9/2000 |
| WO | 2012015722 A1 | 2/2012 |
| WO | 2014022379 A1 | 2/2014 |
| WO | 2014189887 A2 | 11/2014 |
| WO | 2015/142674 A1 | 9/2015 |
| WO | 2015200518 A1 | 12/2015 |
| WO | 2016181318 A1 | 11/2016 |

OTHER PUBLICATIONS

International Search Report and Written Opinion of the International Searching Authority, dated Feb. 2, 2017 for International Application No. PCT/US2016/059345 (10 Pages).
International Search Report and Written Opinion of the International Searching Authority dated Aug. 5, 2015 for International Application No. PCT/US2015/020596 (13 Pages).
International Search Report and Written Opinion of the International Searching Authority dated May 16, 2017 for International Application No. PCT/US2017/015582 (11 pages).
International Search Report and Written Opinion of the International Searching Authority dated May 16, 2017 for International Application No. PCT/US2017/015584 (11 pages).
International Search Report and Written Opinion of the International Searching Authority dated Nov. 29, 2013 or International Application No. PCT/US2013/052703 (11 Pages).
International Search Report and Written Opinion of the International Searching Authority dated Jun. 11, 2017 for International Application No. PCT/US2017/019398 (27 Pages).
"Aquamantys System" Product Brochure, Medtronic, 2014 (12 Pages).
"Starburst Talon" Specifications Brochure, Angiodynamics, 2013 (2 Pages).
Medtronic, "Aquamantys Bipolar Sealers." Electrosurgical Products, Jun. 2017. Retrieved Jul. 21, 2017. <http://www.medtronic.com/us-en/healthcare-professionals/products/general-surgery/electrosurgical/aquamantys-bipolar-sealers.html> (11 Pages).
Non-Final Office Action dated Aug. 11, 2017 for U.S. Appl. No. 15/337,334 (11 Pages).
Response to Non-Final Office Action Filed Sep. 20, 2017 for U.S. Appl. No. 15/337,334 (6 Pages).
Non-Final Office Action dated Aug. 11, 2017 for U.S. Appl. No. 15/624,327 (11 Pages).
Response to Non-Final Office Action Filed Sep. 19, 2017 for U.S. Appl. No. 15/624,327 (8 Pages).
Non-Final Office Action dated Aug. 4, 2017 for U.S. Appl. No. 15/624,230 (18 Pages).
Response to Non-Final Office Action Filed Sep. 20, 2017 for U.S. Appl. No. 15/624,230 (10 Pages).
International Search Report and Written Opinion of the International Searching Authority dated Oct. 19, 2017 for International Application No. PCT/US2017/041501 (63 Pages).
International Search Report and Written Opinion of the Interational Searching Authority dated Feb. 27, 2018 for International Application No. PCT/US2017/056754 (11 Pages).
Extended European Search Report dated Jun. 10, 2016 for European Application No. 13825361.2 (13 Pages).
International Search Report and Written Opinion of the International Searching Authority dated Sep. 16, 2018 for International Application No. PCT/US2018/036268 (11 Pages).
International Search Report and Written Opinion of the International Searching Authority dated Aug. 26, 2018 for International Application No. PCT/US2017/059850 (10 Pages).
International Search Report and Written Opinion dated Jun. 6, 2018 for International Application No. PCT/US2018/019151 (17 Pages).
Notice of Allowance dated Jul. 24, 2018 for U.S. Appl. No. 15/784,778 (12 Pages).
International Search Report and Written Opinion of the International Searching Authority dated Nov. 1, 2018 for International Application No. PCT/US2018/043654 (10 Pages).
International Search Report and Written Opinion of the International Searching Authority dated Nov. 15, 2018 for International Application PCT/US2018/043658 (15 Pages).
Extended European Search Report dated Nov. 27, 2018 for European Application No. 16787228.2 (6 Pages).

* cited by examiner

Insert cannula into cavity
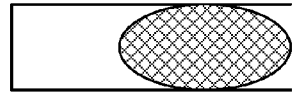
Inner tube pushes stent out with sliding knob
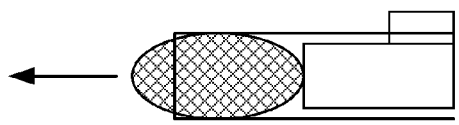
Stent naturally expands when released from cannula
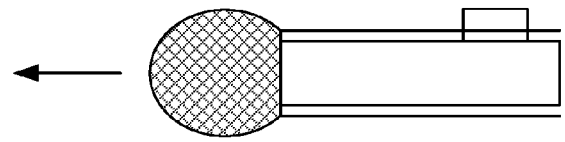
To complete expansion, slide second knob proximally to pull distal part of stent until full spherical shape achieved
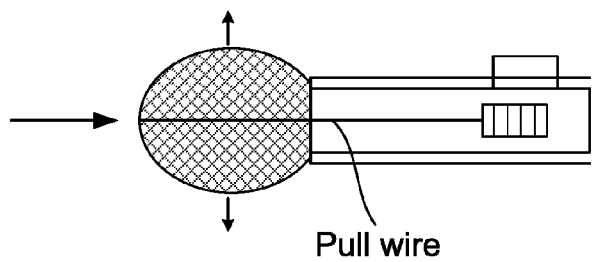
Pull wire
Lock knob into position and start ablation
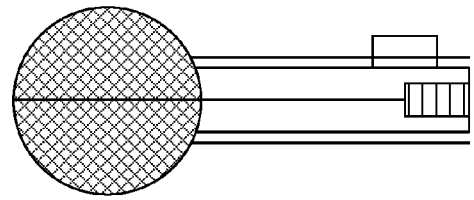
FIG. 10

CAVITARY TISSUE ABLATION

CROSS-REFERENCE TO RELATED APPLICATIONS

This application claims the benefit of, and priority to, U.S. Provisional Application Ser. No. 62/154,377, filed Apr. 29, 2015, the content of which is hereby incorporated by reference herein in its entirety.

FIELD

The present disclosure relates generally to medical devices, and, more particularly, to a tissue ablation device having a deployable applicator head configured to be delivered to a tissue cavity and ablate marginal tissue surrounding the tissue cavity.

BACKGROUND

Cancer is a group of diseases involving abnormal cell growth with the potential to invade or spread to other parts of the body. Cancer generally manifests into abnormal growths of tissue in the form of a tumor that may be localized to a particular area of a patient's body (e.g., associated with a specific body part or organ) or may be spread throughout. Tumors, both benign and malignant, are commonly treated and removed via surgical intervention, as surgery often offers the greatest chance for complete removal and cure, especially if the cancer has not spread to other parts of the body. However, in some instances, surgery alone is insufficient to adequately remove all cancerous tissue from a local environment.

For example, treatment of early stage breast cancer typically involves a combination of surgery and adjuvant irradiation. Unlike a mastectomy, a lumpectomy removes only the tumor and a small rim (area) of the normal tissue around it. Radiation therapy is given after lumpectomy in an attempt to eradicate cancer cells that may remain in the local environment around the removed tumor, so as to lower the chances of the cancer returning. However, radiation therapy as a post-operative treatment suffers various shortcomings. For example, radiation techniques can be costly and time consuming, and typically involve multiple treatments over weeks and sometimes months. Furthermore, radiation often results in unintended damage to the tissue outside the target zone. Thus, rather than affecting the likely residual tissue, typically near the original tumor location, radiation techniques often adversely affect healthy tissue, such as short and long-term complications affecting the skin, lungs, and heart. Accordingly, such risks, when combined with the burden of weeks of daily radiation, may drive some patients to choose mastectomy instead of lumpectomy. Furthermore, some women (e.g., up to thirty percent (30%)) who undergo lumpectomy stop therapy before completing the full treatment due to the drawbacks of radiation treatment. This may be especially true in rural areas, or other areas in which patients may have limited access to radiation facilities.

SUMMARY

Tumors, both benign and malignant, are commonly treated and destroyed via surgical intervention, as surgery often offers the greatest chance for complete removal and cure, especially if the cancer has not metastasized. However, after the tumor is destroyed, a hollow cavity may remain, wherein tissue surrounding this cavity and surrounding the original tumor site can still leave abnormal or potentially cancerous cells that the surgeon fails, or is unable, to excise. This surrounding tissue is commonly referred to as "margin tissue" or "marginal tissue", and is the location within a patient where a reoccurrence of the tumor may most likely occur.

The tissue ablation system of the present disclosure can be used during an ablation procedure to destroy the thin rim of marginal tissue around the cavity in an effort to manage residual disease in the local environment that has been treated. In particular, the present disclosure is generally directed to a cavitary tissue ablation system including an ablation device to be delivered into a tissue cavity and emit non-ionizing radiation, such as radiofrequency (RF) energy, to treat the marginal tissue around the tissue cavity. The ablation device generally includes a probe having a deployable applicator member or head coupled thereto and configured to transition between a collapsed configuration, in which the applicator head can be delivered to and maneuvered within a previously formed tissue cavity (e.g., formed from tumor removal), and an expanded configuration, in which the applicator head is configured to ablate marginal tissue (via RF) immediately surrounding the site of a surgically removed tumor in order to minimize recurrence of the tumor. The tissue ablation device of the present disclosure is configured to allow surgeons, or other medical professionals, to deliver precise, measured doses of RF energy at controlled depths to the marginal tissue surrounding the cavity.

Accordingly, a tissue ablation device consistent with the present disclosure may be well suited for treating hollow body cavities, such as irregularly-shaped cavities in breast tissue created by a lumpectomy procedure. It should be noted, however, that the devices of the present disclosure are not limited to such post-surgical treatments and, as used herein, the phrase "body cavity" may include non-surgically created cavities, such as natural body cavities and passages, such as the ureter (e.g. for prostate treatment), the uterus (e.g. for uterine ablation or fibroid treatment), fallopian tubes (e.g. for sterilization), and the like. Additionally, or alternatively, tissue ablation devices of the present disclosure may be used for the ablation of marginal tissue in various parts of the body and organs (e.g., skin, lungs, liver, pancreas, etc.) and is not limited to treatment of breast cancer.

In one aspect, a tissue ablation device consistent with the present disclosure includes a dual-balloon design. For example, the tissue ablation device includes a probe including a nonconductive elongated shaft having a proximal end and a distal end and at least one lumen extending therethrough, and an expandable balloon assembly coupled to the distal end of the probe shaft. The expandable balloon assembly includes an expandable inner balloon having an inner balloon wall having an exterior surface, an interior surface and a lumen defined therein and in fluid connection with at least one lumen of the probe. The inner balloon is configured to inflate into an expanded configuration in response to delivery of a first fluid from at least one lumen of the probe into the lumen of the inner balloon.

The expandable balloon assembly further includes an expandable outer balloon surrounding the inner balloon and configured to transition to an expanded configuration in response expansion of the inner balloon. The outer balloon includes an outer balloon wall having an interior surface, an exterior surface, and a chamber defined between the interior surface of the outer balloon and the exterior surface of the inner balloon. The exterior surface of the inner balloon wall has an irregular surface defined thereon. In particular, the inner balloon wall may include a plurality of bumps, ridges, or other features arranged on an outer surface thereof configured to maintain separation between the outer surface of the inner balloon wall and the interior surface of the outer balloon wall, thereby ensuring the chamber is maintained.

The chamber defined between the inner surface of the outer balloon wall and the outer surface of the inner balloon wall is in fluid connection with at least one lumen of the probe, so as to receive a second fluid therefrom. The outer balloon wall further includes a plurality of perforations configured to allow the passage of the second fluid from the chamber to the exterior surface of the outer balloon upon delivery of the second fluid from at least one lumen of the probe into the chamber.

The ablation device further includes an electrode array comprising a plurality of conductive wires positioned within the chamber between the exterior surface of the inner balloon wall and the interior surface of the outer balloon wall. Each of the plurality of conductive wires is configured to conduct energy to be carried by the second fluid within the chamber from the interior surface to the exterior surface of the outer balloon wall for ablation of a target tissue. In particular, upon activating delivery of RF energy from the at least one conductive element, the RF energy is transmitted from the conductive element to the exterior surface of the outer balloon by way of fluid weeping from the perforations, thereby creating a virtual electrode. For example, the fluid within the chamber and weeping through the perforations on the outer balloon is a conductive fluid (e.g., saline) and thus able to carry electrical current from an active conductive element. Upon the fluid weeping through the perforations, a pool or thin film of fluid is formed on the exterior surface of the outer balloon and is configured to ablate surrounding tissue via the electrical current carried from the active conductive elements. Accordingly, ablation via RF energy is able to occur on the exterior surface of the outer balloon in a controlled manner and does not require direct contact between tissue and the conductive elements.

In some embodiments, each of the plurality of conductive wires is independent from one another. Thus, in some embodiments, each of the plurality of conductive wires, or one or more sets of a combination of conductive wires, is configured to independently receive an electrical current from an energy source and independently conduct energy. In some embodiments, each of the plurality of conductive wires is configured to conduct energy upon receipt of the electrical current, the energy including RF energy.

In some embodiments, the irregular surface defined on the exterior surface of the inner balloon wall may include a plurality of ridges. The plurality of ridges may generally extend longitudinally along the exterior surface of the inner balloon wall. The plurality of ridges may be configured to make contact with the inner surface of the outer balloon wall to maintain separation between the remaining outer surface of the inner balloon wall and the inner surface of the outer balloon wall. Each of the plurality of conductive wires may further be positioned between two adjacent ridges and one or more of the plurality of perforations of the outer balloon wall may be substantially aligned with an associated one of the plurality of conductive wires.

In some embodiments, the inner balloon may be configured to receive the first fluid from a first lumen of the probe and the outer balloon may be configured to receive the second fluid from a second lumen of the probe. The delivery of the first and second fluids to the inner and outer balloons, respectively, may be independently controllable via a controller, for example. In some embodiments, the first and second fluids are different. In other embodiments, the first and second fluids are the same. In some embodiments, at least the second fluid, which is to be delivered to the chamber and used for creating a virtual electrode in combination with the electrode array, is a conductive fluid, such as saline.

The dual-balloon design is particularly advantageous in that it does not require a syringe pump, and can be supplied with gravity-fed fluid source. In addition, the volume of fluid required within the chamber is significantly less (when compared to a single balloon design), thus less wattage is required to achieve RF ablation.

In another aspect, a tissue ablation device consistent with the present disclosure includes an expandable mesh body configured to deliver energy for tissue ablation. The tissue ablation device includes a probe comprising an elongated shaft having a proximal end and a distal end and at least one lumen providing a pathway extending from the proximal end to the distal end and an expandable mesh assembly coupled to the distal end of the probe. The mesh assembly includes a self-expanding mesh body configured to transition between a collapsed configuration and an expanded configuration. When in the collapsed configuration, the mesh body is received within the at least one lumen of the probe and when in the expanded configuration, the mesh body is deployed from the at least one lumen of the probe and expands into a predefined shape. The mesh body is comprised of an electrically conductive material and configured to conduct and deliver electrical current to target tissue when in the expanded configuration.

In some embodiments, the self-expanding mesh body includes a webbing coating one or more portions of the mesh body, wherein the web comprises a non-conductive material. The webbing is configured to block delivery of electrical current from the one or more portions of mesh body coated with the webbing.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

Figure 1:
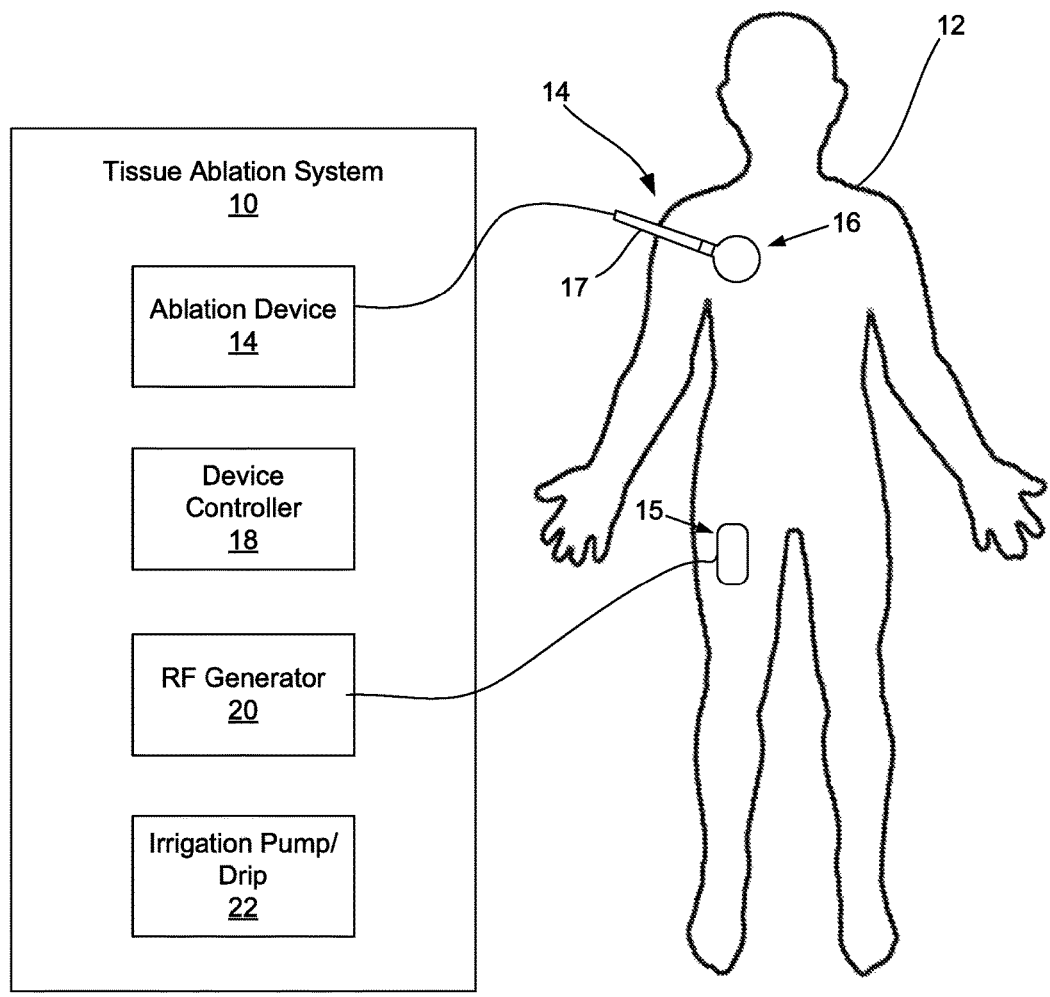
FIG. 1 is a schematic illustration of an ablation system consistent with the present disclosure.
Figure 3:
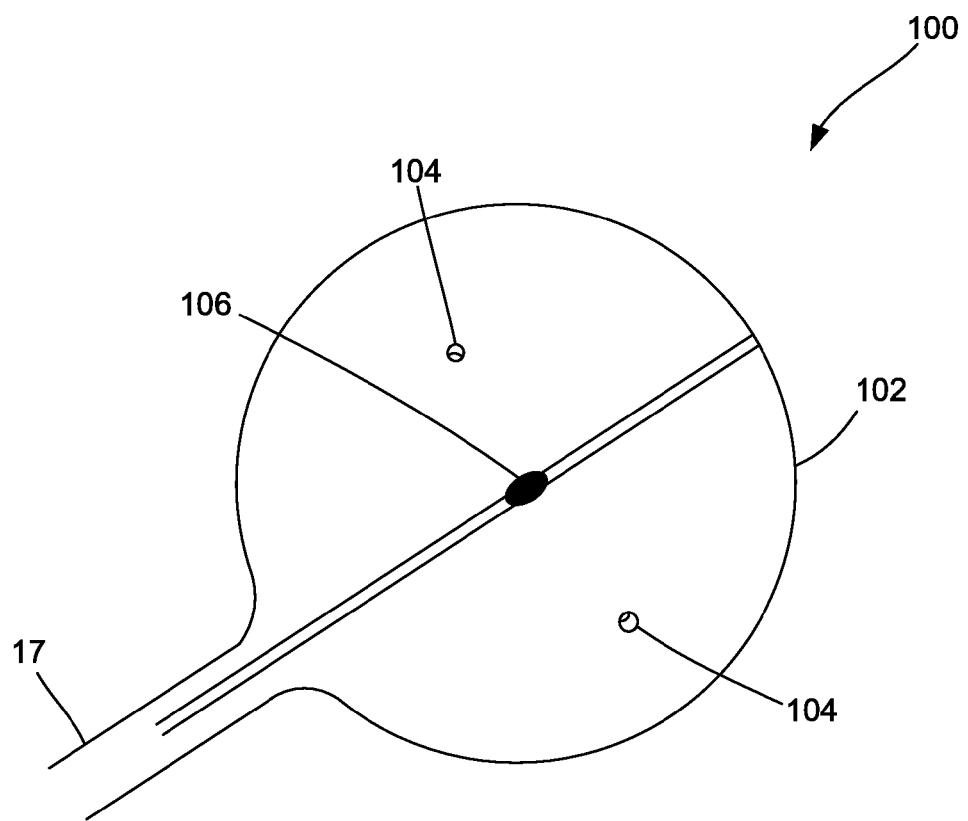
FIG. 3 is a perspective view, partly in section, of one embodiment of an applicator head compatible with the tissue ablation device of FIG. 1.
Figure 4:
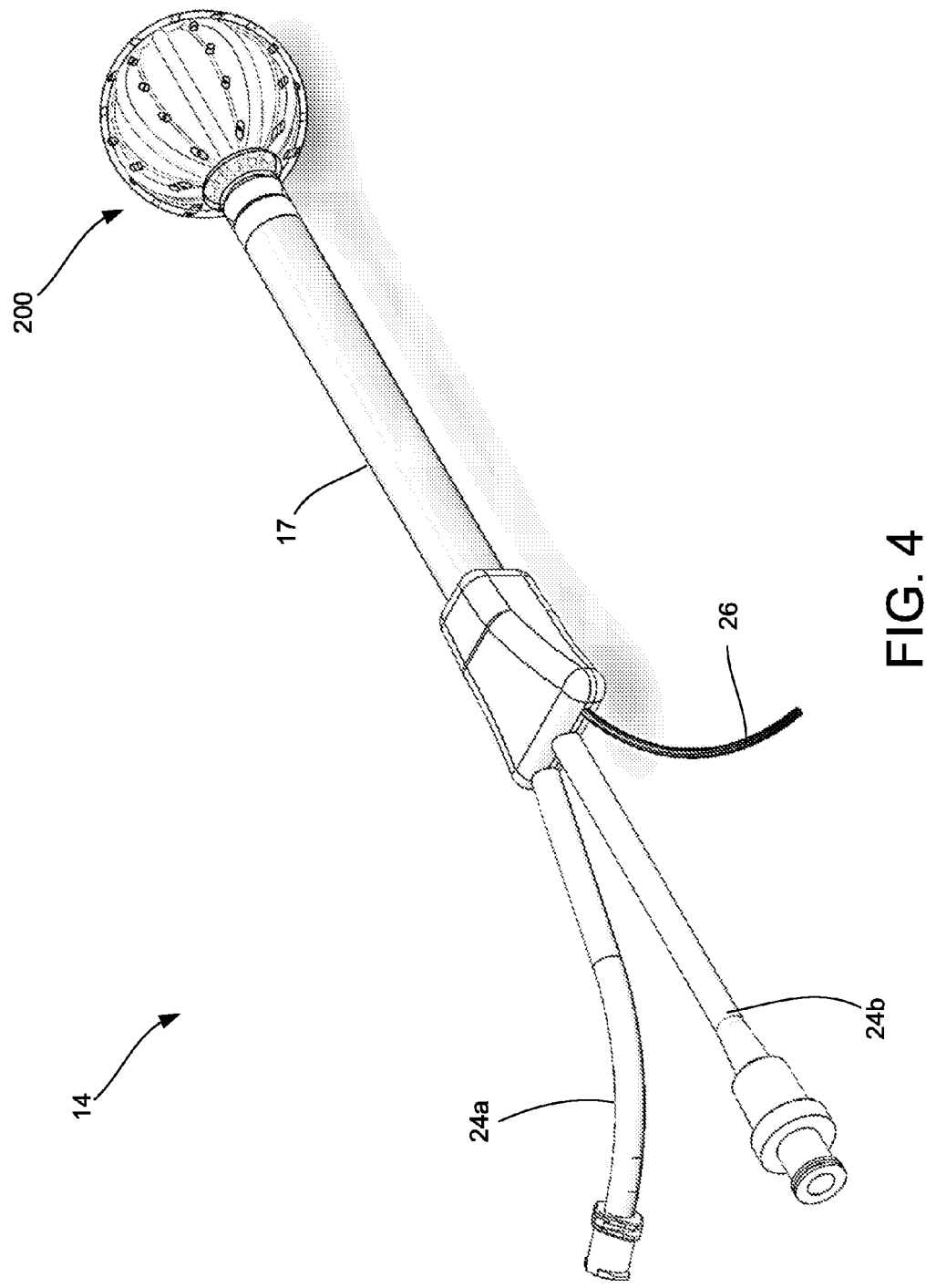
FIG. 4 is a perspective view of another embodiment of an applicator head compatible with the tissue ablation device of FIG. 1.
Figure 6:
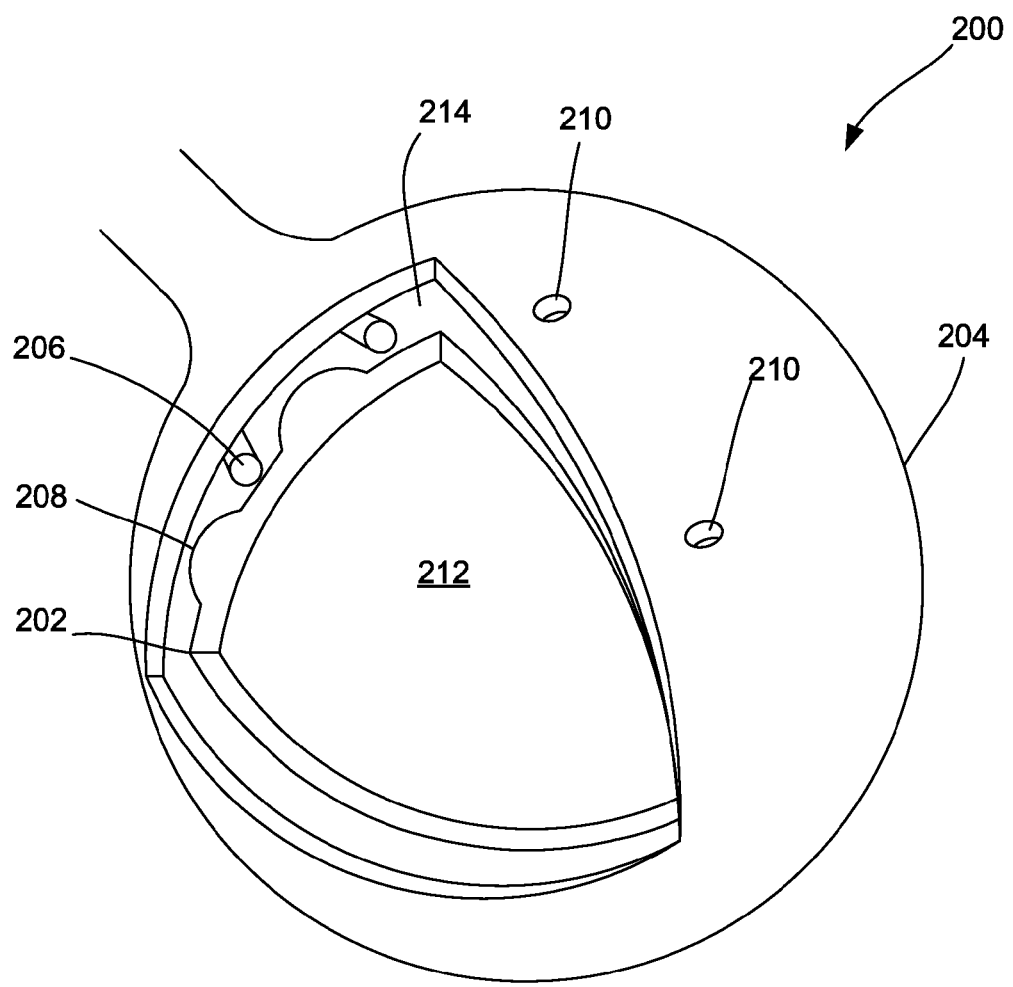
Figure 7A:
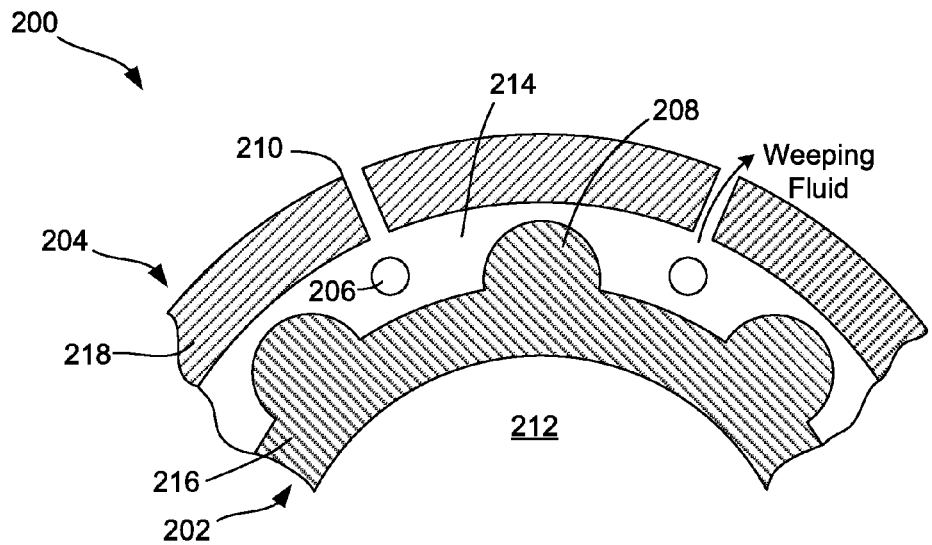
Figure 7B:
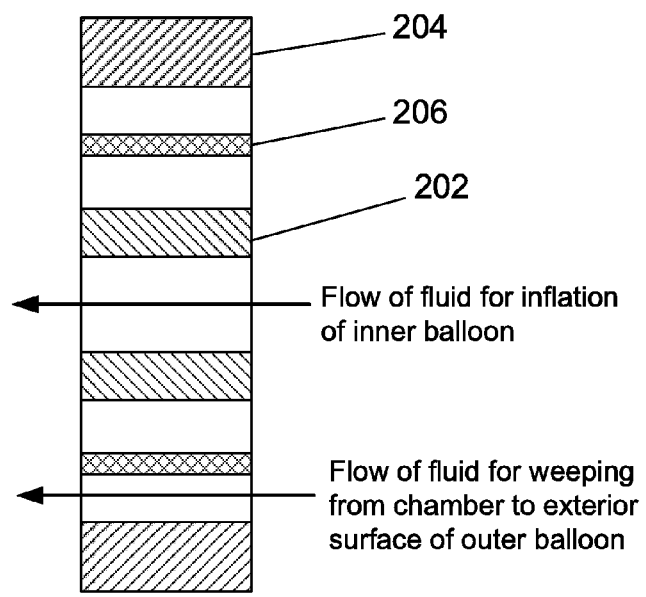
Figure 8:
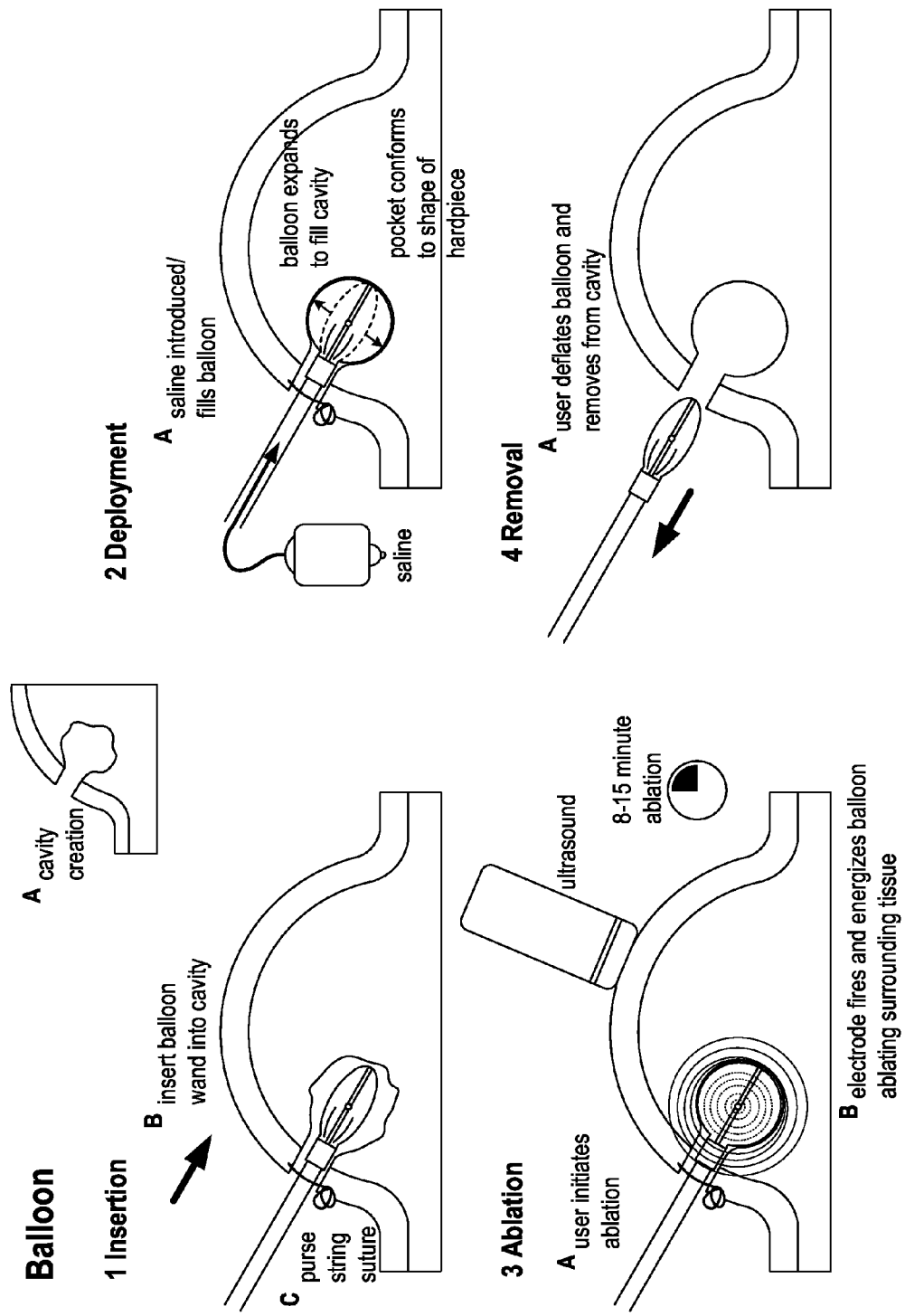
Figure 9:
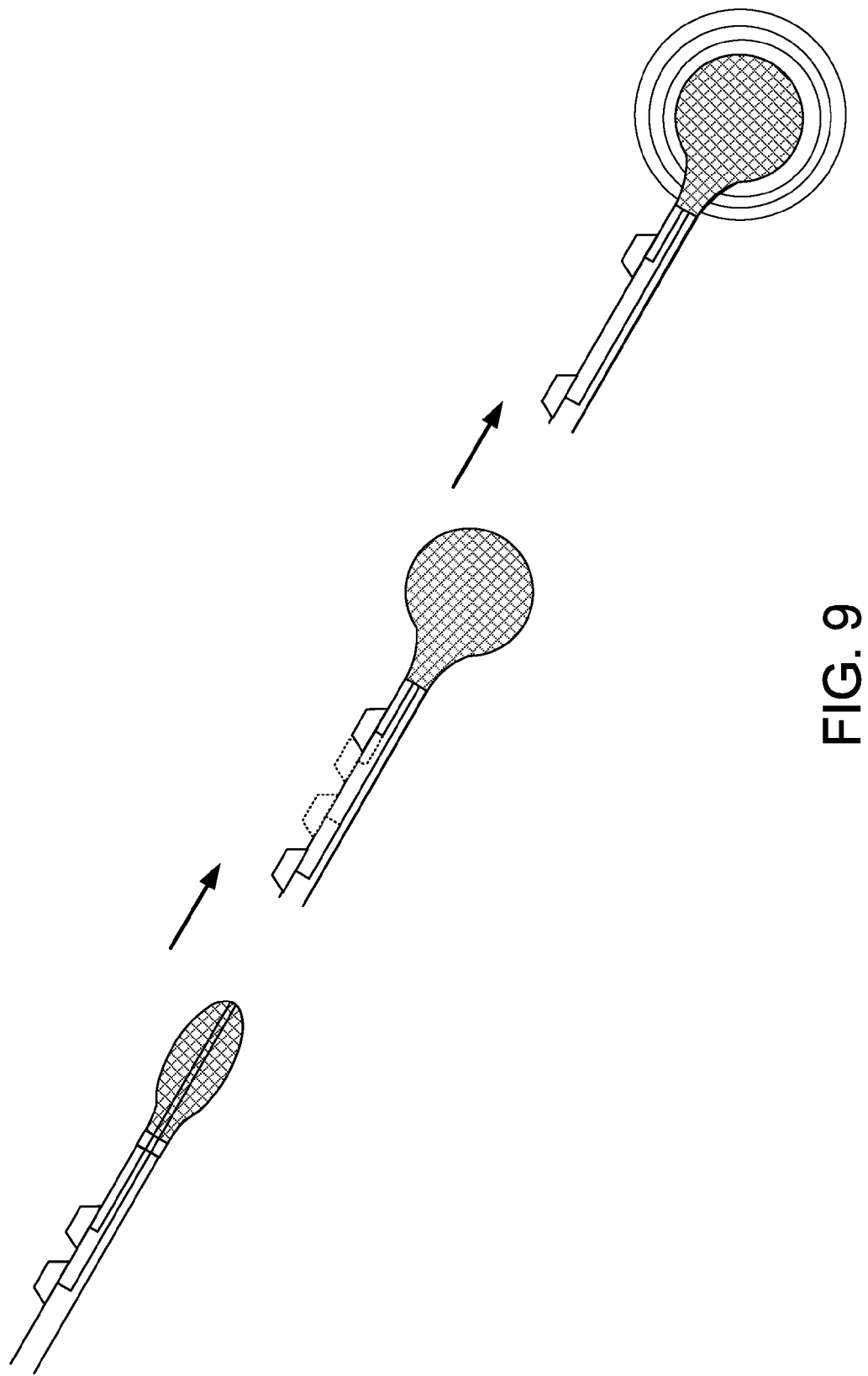
Figure 11:
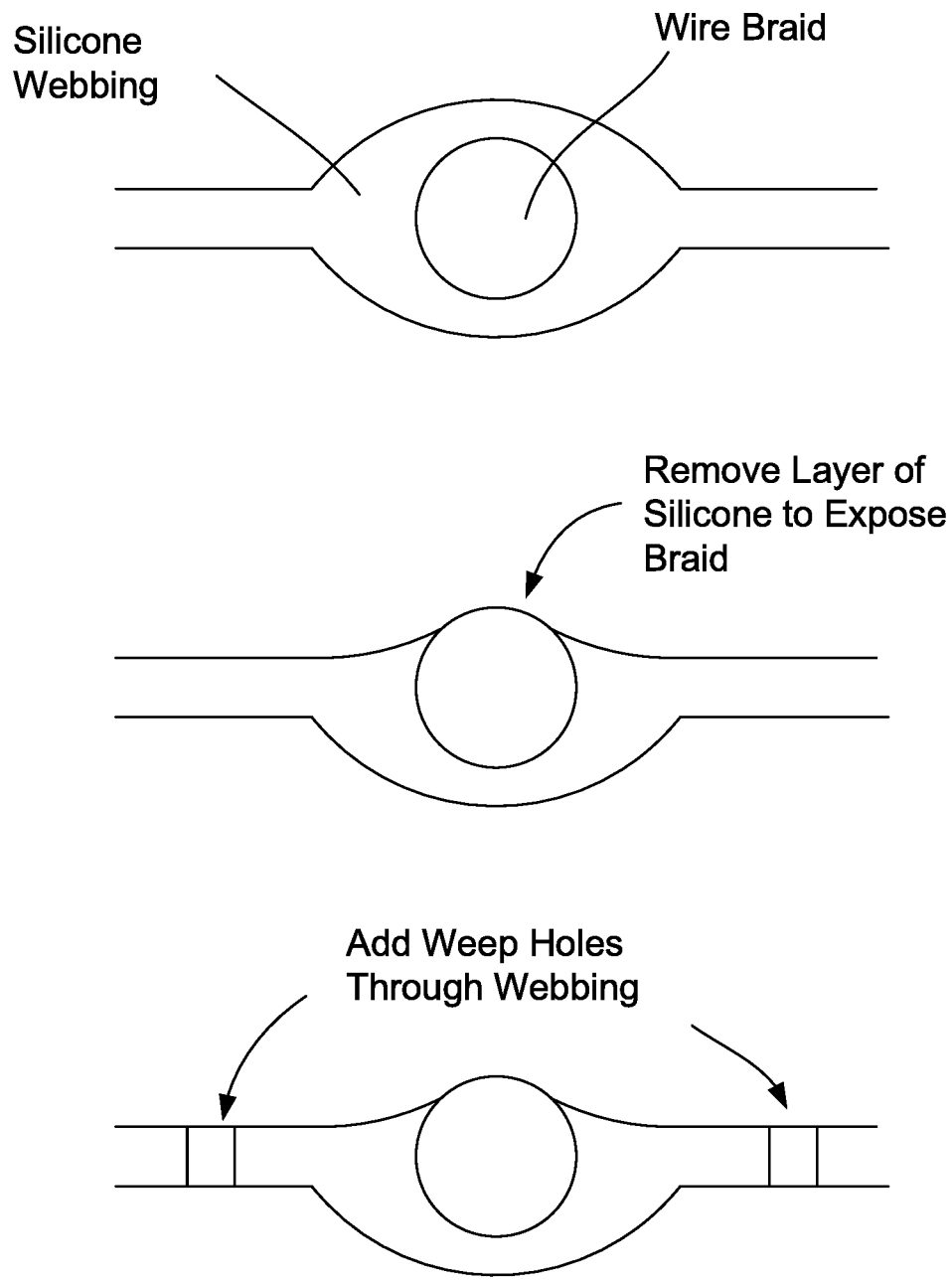
Figure 12:
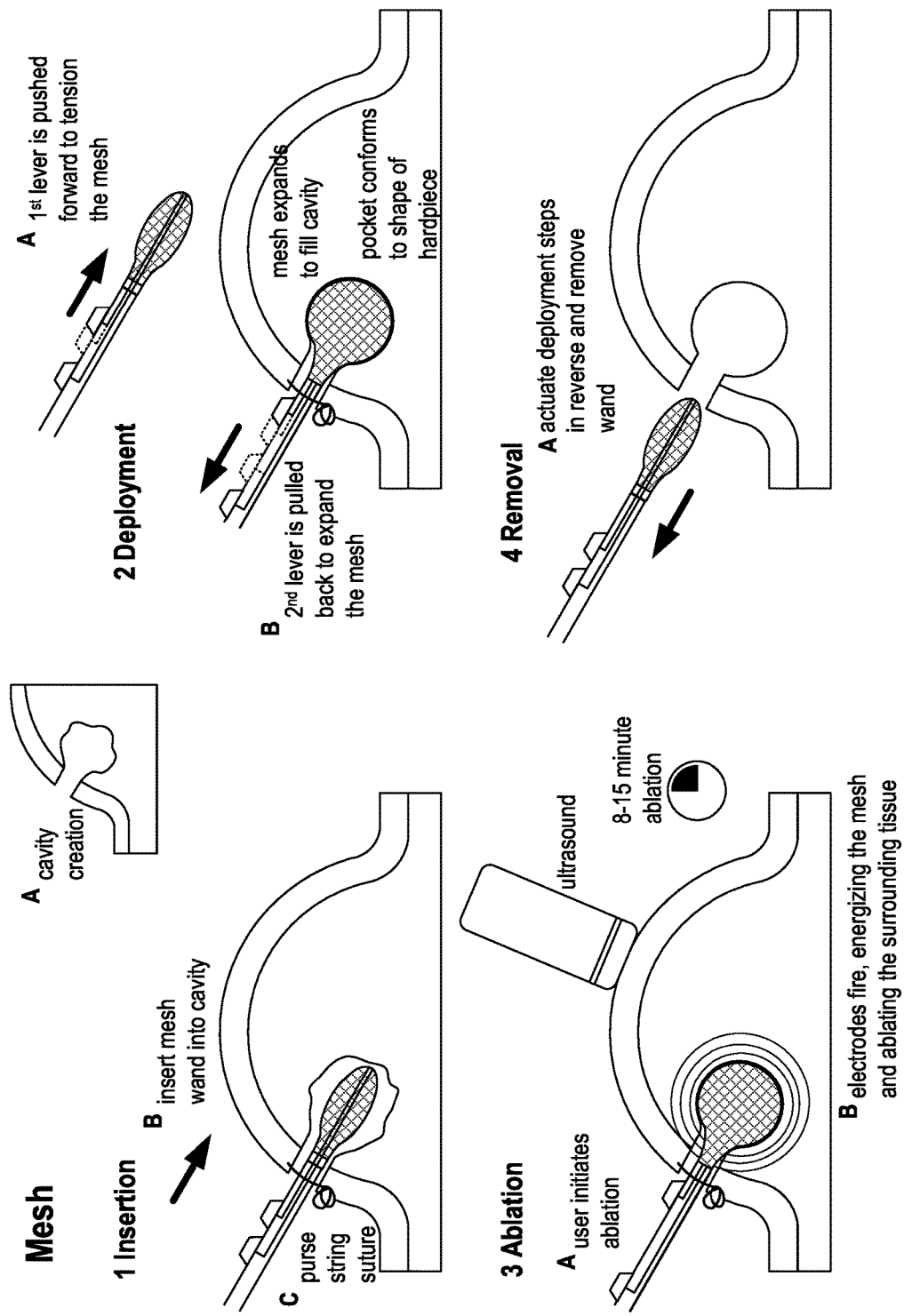

FIG. is a perspective view, partly in section, of the applicator head of FIG. 4;

FIGS. 7A and 7B are sectional views of a portion of the applicator head of FIG. 6 illustrating the arrangement of components relative to one another;

FIG. 8 is a schematic illustration of the delivery of the applicator head of FIG. 3 into a tissue cavity and subsequent ablation of marginal tissue according to methods of the present disclosure;

FIG. 9 is a perspective view of another embodiment of an applicator head compatible with the tissue ablation device of FIG. 1;

FIG. 10 illustrates a method of deploying the applicator head of FIG. 9 into an expanded configuration for delivery of RF energy to a target site for ablation of marginal tissue;

FIG. 11 illustrates different embodiments of the outer surface of the applicator head of FIG. 9; and FIG. 12 is a schematic illustration of the delivery of the applicator head of FIG. 9 into a tissue cavity and subsequent ablation of marginal tissue according to methods of the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a tissue ablation device having a deployable applicator head configured to be delivered into a tissue cavity and ablate marginal tissue surrounding the tissue cavity.

The tissue ablation system of the present disclosure can be used during an ablation procedure to destroy the thin rim of marginal tissue around the cavity in an effort to manage residual disease in the local environment that has been treated. In particular, the present disclosure is generally directed to a cavitary tissue ablation system including an ablation device to be delivered into a tissue cavity and emit non-ionizing radiation, such as radiofrequency (RF) energy, to treat the marginal tissue around the tissue cavity. The ablation device generally includes a probe having a deployable applicator head coupled thereto and configured to transition between a collapsed configuration, in which the applicator head can be delivered to and maneuvered within a previously formed tissue cavity (e.g., formed from tumor removal), and an expanded configuration, in which the applicator head is configured to ablate marginal tissue (via RF) immediately surrounding the site of a surgically removed tumor in order to minimize recurrence of the tumor. The tissue ablation device of the present disclosure is configured to allow surgeons, or other medical professionals, to deliver precise, measured doses of RF energy at controlled depths to the marginal tissue surrounding the cavity.

Accordingly, a tissue ablation device consistent with the present disclosure may be well suited for treating hollow body cavities, such as irregularly-shaped cavities in breast tissue created by a lumpectomy procedure. It should be noted, however, that the devices of the present disclosure are not limited to such post-surgical treatments and, as used herein, the phrase "body cavity" may include non-surgically created cavities, such as natural body cavities and passages, such as the ureter (e.g. for prostate treatment), the uterus (e.g. for uterine ablation or fibroid treatment), fallopian tubes (e.g. for sterilization), and the like. Additionally, or alternatively, tissue ablation devices of the present disclosure may be used for the ablation of marginal tissue in various parts of the body and organs (e.g., skin, lungs, liver, pancreas, etc.) and is not limited to treatment of breast cancer.

FIG. 1 is a schematic illustration of an ablation system 10 for providing ablation of marginal tissue during a tumor removal procedure in a patient 12. The ablation system 10 generally includes an ablation device 14, which includes a probe having a deployable applicator member or head 16 and an elongated catheter shaft 17 to which the deployable applicator head 16 is connected. The catheter shaft 17 may generally include a nonconductive elongated member including a fluid delivery lumen. The ablation device 14 may further be coupled to a device controller 18 and an ablation generator 20 over an electrical connection, and an irrigation pump or drip 22 over a fluid connection. As will be described in greater detail herein, the device controller 18 may be used to control the emission of energy from one or more conductive elements of the device 14 to result in ablation, as well as controlling the delivery of fluid to or from the deployable applicator head 16 so as to control the expansion and collapse of the head 16. In some cases, the device controller 18 may be housed within the ablation device 14. The ablation generator 20 may also connected to a return electrode 15 that is attached to the skin of the patient 12.

As will be described in greater detail herein, during an ablation treatment, the ablation generator 20 may generally provide RF energy (e.g., electrical energy in the radiofrequency (RF) range (e.g., 350-800 kHz)) to an electrode array of the ablation device 14, as controlled by the device controller 18. At the same time, saline may also be released from the head 16. The RF energy travels through the blood and tissue of the patient 12 to the return electrode 15 and, in the process, ablates the region(s) of tissues adjacent to portions of the electrode array that have been activated.

Figure 2:
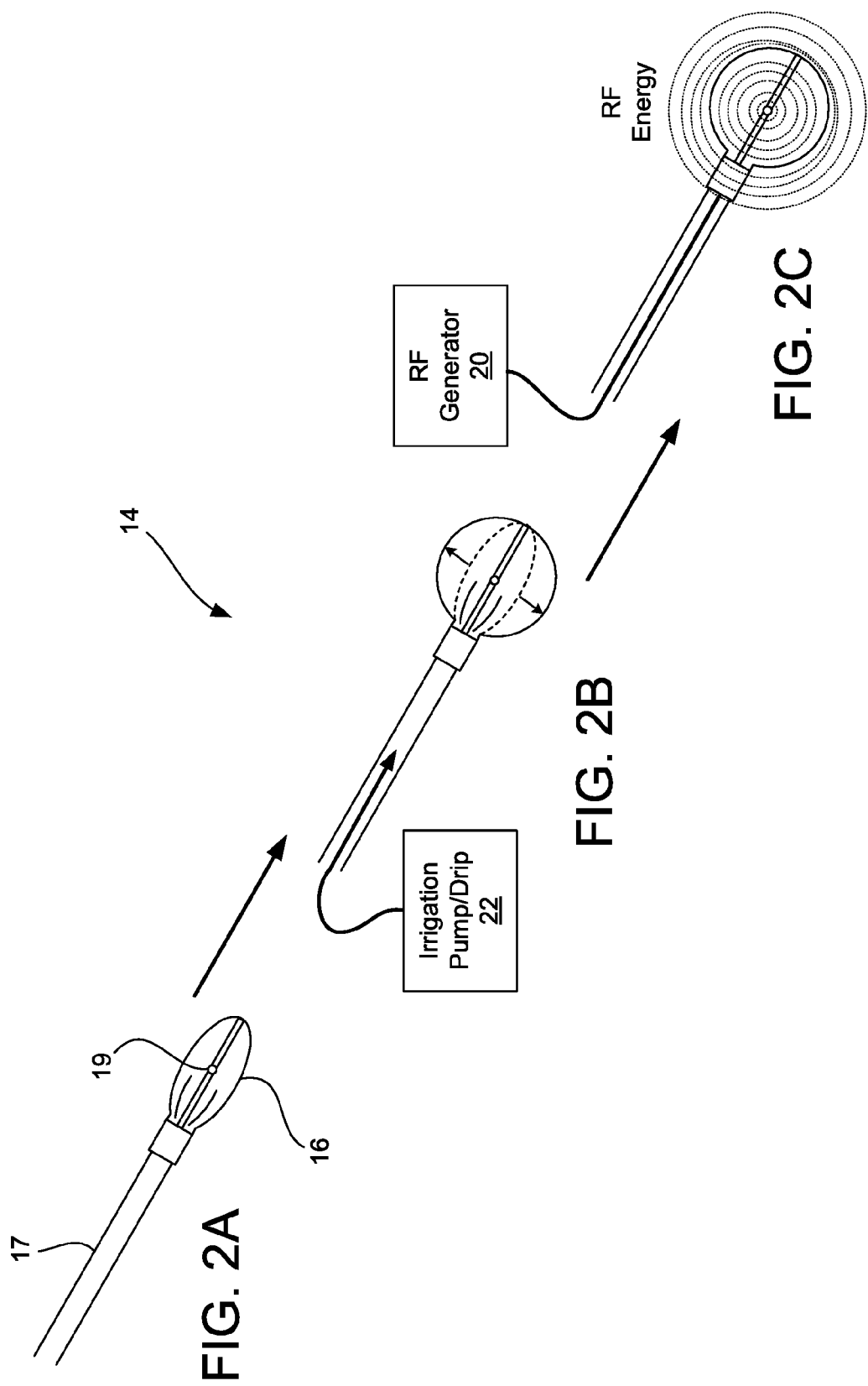
FIGS. 2A-2C are perspective views of an exemplary embodiment of a tissue ablation device including an expandable applicator head configured to transition between collapsed and expanded configurations and to ablate marginal tissue.

Turning to FIGS. 2A-2C, one embodiment of an exemplary tissue ablation device configured to ablate marginal tissue is shown. The tissue ablation devices of the present disclosure generally include a probe including a shaft 17 having a proximal end and a distal end, wherein the applicator head 16 is positioned at the distal end. In some embodiments, the shaft 17 of the probe may generally resemble a catheter and thus may further include at least one lumen for providing a pathway from the proximal end of the shaft to the distal end of the shaft and the applicator head so as to allow various components to be in fluid communication with the applicator head.

For example, in one embodiment, the applicator head includes at least one balloon configured to transition from a collapsed configuration to an expanded configuration in response to delivery of a fluid thereto. FIGS. 2A-2C illustrate the applicator head 16 transitioning from a collapsed configuration (FIG. 2A) to an expanded configuration (FIG. 2B) via delivery of a fluid to the head 16 and activated to emit energy for ablation of tissue (FIG. 2C). The at least one lumen of the shaft 17 may provide a fluid pathway from the proximal end, which may be coupled to a fluid source (i.e., irrigation pump or drip 22), and the interior volume of the balloon 16. Furthermore, as will be described in greater detail herein, the tissue ablation devices of the present disclosure further include a conductive element 19 (e.g., an electrode) positioned within the applicator head 16 and configured to deliver RF energy for the ablation of marginal tissue. Accordingly, the probe may be coupled to an RF generator 20, for example, by way of an electrical connection at the proximal end, and wiring may pass through the at least one lumen of the shaft 17 to the conductive element 19. Further, in another embodiment, the applicator head may include a self-expanding mesh-like conductive element configured to deliver RF energy upon delivery to the target site. Accordingly, one or more control wires or other components may be coupled to the mesh-like conductive element to control the retraction and expansion (e.g., via pushing and pulling) of the mesh-like conductive element from the shaft of the probe, as well as electrical wiring for electrically coupling the conductive element and RF generator, wherein such control and electrical wires may be housed within the at least one lumen of the shaft of the probe.

Accordingly, in some embodiments, the shaft 17 of the probe may be configured as a handle adapted for manual manipulation. It should be noted, however, that in other embodiments, the shaft may be configured for connection to and/or interface with a surgical robot, such as the Da Vinci® surgical robot available from Intuitive Surgical, Inc., Sunnyvale, Calif. In all cases, the shaft may be configured to be held in place by a shape lock or other deployment and suspension system of the type that is anchored to a patient bed and which holds the probe in place while the ablation or other procedure takes place, eliminating the need to a user to manually hold the device for the duration of the treatment.

FIG. 3 is a perspective view, partly in section, of one embodiment of an applicator head 100 compatible with the tissue ablation device 14 of FIG. 1. As shown, the applicator head 100 includes an inflatable balloon 102 having a plurality of perforations 104, holes, or micropores, so as to allow a fluid provided within the balloon 102, such as saline, to pass therethrough, or weep, from the balloon 102 when the balloon 102 is inflated. The perforations 104 may be sized, shaped, and/or arranged in such a pattern so as to allow a volume of fluid to pass from the interior volume of the balloon to an exterior surface of the balloon at a controlled rate so as to allow the balloon to remain inflated and maintain its shape.

As previously described, the probe further includes a conductive element 106, such as an electrode, positioned within the balloon, wherein the electrode 106 is coupled to an RF energy source 20. When in the collapsed configuration (e.g., little or no fluid within the interior volume) (shown in FIG. 2A), the balloon has a smaller size or volume than when the balloon is in the expanded configuration. Once positioned within the target site (e.g., tissue cavity), fluid may then be delivered to the balloon so as to inflate the balloon into an expanded configuration (shown in FIG. 2B), at which point, ablation of marginal tissue can occur. In particular, an operator (e.g., surgeon) may initiate delivery of RF energy from the conductive element 106 by using the controller 18, and RF energy is transmitted from the conductive element 106 to the outer surface of the balloon 102 by way of the fluid weeping from the perforations 104. Accordingly, ablation via RF energy is able to occur on the exterior surface (shown in FIG. 2C). More specifically, upon activating delivery of RF energy from the conductive element (electrode), the RF energy is transmitted from the conductive element to the outer surface of the balloon by way of the fluid weeping from the perforations, thereby creating a virtual electrode. For example, the fluid within the interior of the balloon 102 and weeping through the perforations 104 to the outer surface of the balloon 102 is a conductive fluid (e.g., saline) and thus able to carry electrical current from the active electrode 106. Accordingly, upon the fluid weeping through the perforations 104, a pool or thin film of fluid is formed on the exterior surface of the balloon 102 and is configured to ablate surrounding tissue via the electrical current carried from the active electrode 106. Accordingly, ablation via RF energy is able to occur on the exterior surface of the balloon in a controlled manner and does not require direct contact between tissue and the electrode 106.

Figure 5:
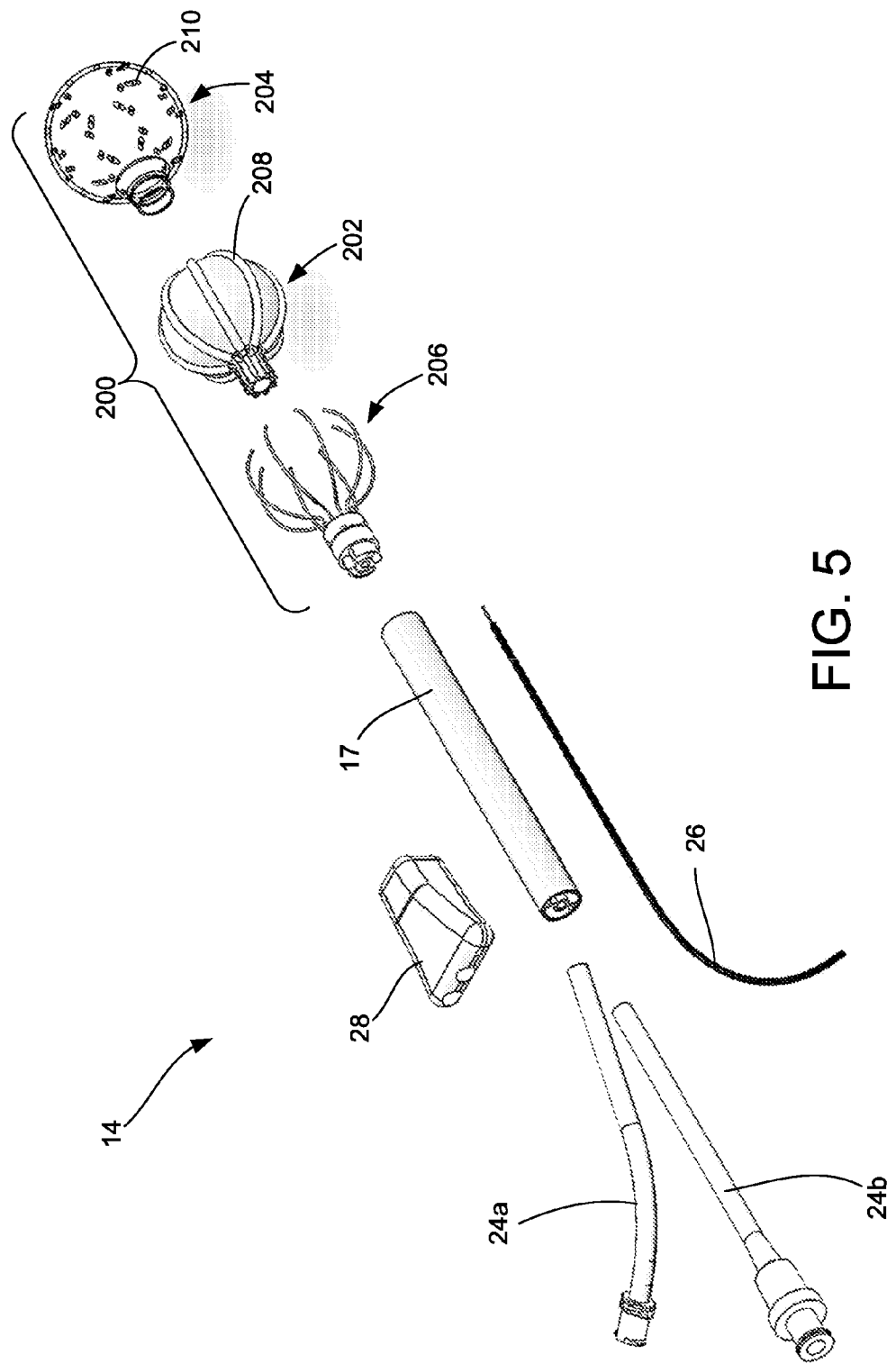
FIG. 5 is an exploded view of the applicator head of FIG. 4.

FIG. 4 is a perspective view of another embodiment of an applicator head 200 compatible with the tissue ablation device 14 and FIG. 5 is an exploded view of the applicator head 200 of FIG. 4. As shown, the applicator head 200 includes a multiple-balloon design. For example, the applicator head 200 includes an inner balloon 202 coupled to a first fluid source via a first fluid line 24a and configured to inflate into an expanded configuration in response to the delivery of fluid (e.g., saline) thereto. The applicator head 200 further includes an outer balloon 204 surrounding the inner balloon 202 and configured to correspondingly expand or collapse in response to expansion or collapse of the inner balloon 202.

The inner balloon 202 may include an irregular outer surface 208, which may include a plurality of bumps, ridges, or other features, configured to maintain separation between the outer surface of the inner balloon 202 and an interior surface of the outer balloon 204, thereby ensuring that a chamber is maintained between the inner and outer balloons. The outer balloon 204 may be coupled to a second fluid source (or the first fluid source) via a second fluid line 24b. The outer balloon 204 may further include a plurality of perforations or holes 210 so as to allow fluid from the second fluid source to pass therethrough, or weep, from the outer balloon 204. The perforations may be sized, shaped, and/or arranged in such a pattern so as to allow a volume of fluid to pass from the chamber to an exterior surface of the outer balloon at a controlled rate.

The applicator head 200 further includes one or more conductive elements, generally resembling electrically conductive wires or tines 206, positioned within the chamber area between the inner balloon 202 and outer balloon 204. The conductive elements 206 are coupled to the RF generator 20 via an electrical line 26, and configured to conduct electrical current to be carried by the fluid within the chamber from the interior surface to the exterior surface of the outer balloon 204 for ablation of a target tissue, as will be described in greater detail herein. It should be noted that in one embodiment, the plurality of conductive wires 206 may be electrically isolated and independent from one another. This design allows for each conductive wire to receive energy in the form of electrical current from a source (e.g., RF generator) and emit RF energy in response. The system may include a device controller 18, for example, configured to selectively control the supply of electrical current to each of the conductive wires 206.

FIG. 6 is a perspective view, partly in section, of the applicator head 200 illustrating compatible with the tissue ablation device of FIG. 1. FIGS. 7A and 7B are sectional views of a portion of the applicator head 200 illustrating the arrangement of components relative to one another.

As shown in FIG. 6, the inner and outer balloons include a chamber 214 defined there between. In particular, the plurality of bumps or ridges 208 arranged on an outer surface of the inner balloon 202 are configured to maintain separation between the outer surface of the inner balloon 202 and an interior surface of the outer balloon 204, thereby ensuring the chamber 214 is maintained.

Once positioned within the target site, a first fluid may be delivered to a lumen 212 of the inner balloon 202, so as to inflate the inner balloon 202 into an expanded configuration, at which point, the outer balloon 204 further expands. A second fluid may then be delivered to the outer balloon 204 such that the second fluid flows within the chamber 214 between the inner and outer balloons 202, 204 and weeps from the outer balloon 204 via the perforations 210. Upon activating delivery of RF energy from the conductive elements 206, the RF energy is transmitted from the conductive elements 206 to the outer surface of the outer balloon 204 by way of the fluid weeping from the perforations 210, thereby creating a virtual electrode. For example, the fluid within the chamber 214 and weeping through the perforations 210 on the outer balloon 204 is a conductive fluid (e.g., saline) and thus able to carry electrical current from the active conductive elements 206. Accordingly, upon the fluid weeping through the perforations 210, a pool or thin film of fluid is formed on the exterior surface of the outer balloon 204 and is configured to ablate surrounding tissue via the electrical current carried from the active conductive elements 206. Accordingly, ablation via RF energy is able to occur on the exterior surface of the outer balloon 204 in a controlled manner and does not require direct contact between tissue and the conductive elements 206.

This embodiment is particularly advantageous in that the dual-balloon design does not require a syringe pump, and can be supplied with gravity-fed fluid source 22. In addition, the volume of fluid required within the chamber is significantly less (when compared to a single balloon design), thus less wattage is required to achieve RF ablation. Another advantage of the dual-balloon design of applicator head 200 is that it is not limited to placement within tissue cavities. Rather, when in a collapsed state, the applicator head 200 is shaped and/or sized to fit through working channels of scopes or other access devices, for example, and thus be used for ablation in a plurality of locations within the human body.

It should be further noted that the device 14 of the present disclosure, including the applicator head 200, may further be equipped with feedback capabilities. For example, while in a deflated, collapsed configuration, and prior to saline flow, the head 200 may be used for the collection of initial data (e.g., temperature and conductivity measurements (impedance measurements) from one or more of the conductive elements 206. Then, upon carrying out the ablation procedure, after certain time ablating, saline flow may be stopped (controlled via controller 18), and subsequent impedance measurements may be taken. The collection of data prior and during an ablation procedure may be processed by the controller 18 so as to provide an estimation of the state of the tissue during an RF ablation procedure, thereby providing an operator (e.g., surgeon) with an accurate indication success of the procedure.

FIG. 8 is a schematic illustration of the delivery of the applicator head 100 of FIG. 3 into a tissue cavity and subsequent ablation of marginal tissue according to methods of the present disclosure.

FIG. 9 is a perspective view of another embodiment of an applicator head compatible with the tissue ablation device of FIG. 1. FIG. 10 illustrates a method of deploying the applicator head of FIG. 9 into an expanded configuration for delivery of RF energy to a target site for ablation of marginal tissue. FIG. 11 illustrates different embodiments of the outer surface of the applicator head of FIG. 9.

As shown, the applicator head may include a silicone-webbed mesh body composed of an electrically conductive material. The mesh body may be self-expanding such that it is able to transition from a collapsed configuration, in which the mesh body is retracted within a portion of the shaft of the probe, to an expanded configuration upon deployment from the shaft of the probe. Accordingly, the mesh body may include a shape-memory alloy, or similar material, so as to allow the mesh body to transition between collapsed and expanded configurations. The mesh body is further composed of an electrically conductive material and coupled to an RF generator, such that the mesh body is configured to deliver RF energy. The mesh body may include webbing material that is applied via a dipping method, for example, such that certain portions of the coated mesh body can be exposed with a solvent, thereby enabling RF energy to be delivered through the mesh to a tissue surface when the mesh body is in the expanded configuration and in direct contact with tissue. In some embodiments, to enhance the ablation, perforations along the webbing may further allow fluid to be delivered to the outer surface of the mesh body. Since the mesh body is able to naturally expand, a fluid (e.g., saline) can be delivered via a gravity-fed bag, and no pump is needed. In some embodiments, an inner balloon may be included within the mesh body so as to reduce the volume of energized saline.

FIG. 12 is a schematic illustration of the delivery of the applicator head of FIG. 9 into a tissue cavity and subsequent ablation of marginal tissue according to methods of the present disclosure.

Accordingly, a tissue ablation devices, particularly the applicator heads described herein, may be well suited for treating hollow body cavities, such as irregularly-shaped cavities in breast tissue created by a lumpectomy procedure. The devices, systems, and methods of the present disclosure can help to ensure that all microscopic disease in the local environment has been treated. This is especially true in the treatment of tumors that have a tendency to recur.

As used in any embodiment herein, the term "controller", "module", "subsystem", or the like, may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The controller or subsystem may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions. Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A medical device, comprising:
    a handle;
    an expandable balloon assembly extending from the handle, the expandable balloon assembly comprising:
        an expandable inner balloon configured to transition from a collapsed configuration to an expanded spherical shape, an exterior surface of the inner balloon including a plurality of ridges defined thereon and oriented generally along a longitudinal axis of the inner balloon and the handle; and
        an expandable outer balloon configured to correspondingly transition from a collapsed configuration to an expanded spherical shape in response to expansion of the inner balloon, the outer balloon comprising a plurality of chambers wherein each chamber is defined between an interior surface of the outer balloon and the exterior surface of the inner balloon and a pair of adjacent ridges of the plurality of ridges, the outer balloon further comprising a plurality of perforations configured to allow passage of a fluid from the plurality of chambers to an exterior surface of the outer balloon; and
    a plurality of conductive wires, each of the plurality of conductive wires:
        disposed within a separate one of the chambers;
        having a length extending from a proximal end of the separate one of the chambers to a distal end of the conductive wire that terminates adjacent to a distal end of the separate one of the chambers;
        including a substantially constant cross section along the length; and
        configured to receive an electrical current and conduct energy to be carried by the fluid passing from the separate one of the chambers to the exterior surface of the outer balloon via the plurality of perforations.

2. The medical device of claim 1, wherein each of the plurality of conductive wires, or one or more sets of a combination of the plurality of conductive wires, is configured to independently receive the electrical current from an energy source and independently conduct the energy.

3. The medical device of claim 1, wherein each of the plurality of conductive wires is configured to conduct the energy, wherein the energy is radiofrequency (RF) energy.

4. The medical device of claim 1, wherein each of the plurality of conductive wires is substantially aligned with one of the plurality of perforations of the outer balloon.

5. The medical device of claim 1, wherein the inner and outer balloons comprise a non-conductive material.

* * * * *